(12) United States Patent
Colombo et al.

(10) Patent No.: US 11,602,509 B2
(45) Date of Patent: Mar. 14, 2023

(54) SALT OF CYSTEAMINE FOR THE PREPARATION OF HIGHLY RESPIRABLE PARTICLES

(71) Applicant: RECORDATI INDUSTRIA CHIMICA E FARMACEUTICA SPA, Milan (IT)

(72) Inventors: Paolo Colombo, Parma (IT); Alessandra Rossi, Parma (IT); Greta Adorni, Noceto (IT); Marco Barchielli, Arese (IT)

(73) Assignee: RECORDATI INDUSTRIA CHIMICA E FARMACEUTICA SPA, Milan (IT)

( * ) Notice: Subject to any disclaimer, the term of this patent is extended or adjusted under 35 U.S.C. 154(b) by 239 days.

(21) Appl. No.: 17/050,875

(22) PCT Filed: May 17, 2019

(86) PCT No.: PCT/EP2019/062872
§ 371 (c)(1),
(2) Date: Oct. 27, 2020

(87) PCT Pub. No.: WO2019/224130
PCT Pub. Date: Nov. 28, 2019

(65) Prior Publication Data
US 2021/0236439 A1    Aug. 5, 2021

(30) Foreign Application Priority Data
May 22, 2018   (EP) ..................................... 18425038

(51) Int. Cl.
*A61K 31/145* (2006.01)
*A61K 9/00* (2006.01)
*A61K 9/16* (2006.01)

(52) U.S. Cl.
CPC .......... *A61K 31/145* (2013.01); *A61K 9/0075* (2013.01); *A61K 9/1652* (2013.01)

(58) Field of Classification Search
None
See application file for complete search history.

(56) References Cited

U.S. PATENT DOCUMENTS

2017/0348254 A1   12/2017   O'Neil

FOREIGN PATENT DOCUMENTS

| CN | 101367884 A | 2/2009 |
|---|---|---|
| TW | 200930385 A | 7/2009 |
| WO | 2009036906 A1 | 3/2009 |
| WO | 2018083326 A1 | 5/2018 |

OTHER PUBLICATIONS

International Search Report and Written Opinion for Corresponding International Application No. PCT/EP2019/062872 (12 Pages) (Jul. 5, 2019).

*Primary Examiner* — Robert T. Crow
*Assistant Examiner* — John P Nguyen
(74) *Attorney, Agent, or Firm* — Lucas & Mercanti, LLP

(57) ABSTRACT

An inhalable microparticles having cysteamine hyaluronate salt is provided. Also a preparation method and a pharmaceutical composition thereof are provided.

17 Claims, 7 Drawing Sheets a)

b)

a)

b)

c)

d)

SALT OF CYSTEAMINE FOR THE PREPARATION OF HIGHLY RESPIRABLE PARTICLES

CROSS-REFERENCE TO RELATED APPLICATIONS

This application is a 371 of PCT/EP2019/062872, filed May 17, 2019, which claims the benefit of European Patent Application No. 18425038.9, filed May 22, 2018.

FIELD OF THE INVENTION

Cysteamine is an active ingredient known to be useful for the treatment of cystinosis. To date, several pharmaceutical products such as Cystagon® (capsules of cysteamine bitartrate), Procysbi® (gastro-resistant capsules of cysteamine bitartrate) and Cystadrops® (cysteamine hydrochloride ophthalmic drops) have been authorized in Europe with this therapeutic indication.

BACKGROUND OF THE INVENTION

In relatively recent times, cysteamine has been granted an orphan designation for cystic fibrosis. Cystic fibrosis (CF) is a hereditary disease that affects the cells in the lungs and the glands in the intestine/pancreas which secrete fluids such as mucus or digestive juices, respectively. As a consequence, these fluids become thick and viscous, blocking both the airways and the flow of digestive juices. This leads not only to problems with the digestion and absorption of food but, even worst, in long-term infection and inflammation of the lungs. Due to the decline in lung function, exacerbations or episodes of acute worsening of CF lung symptoms, often as a result of bacterial infection, are the principle cause of morbidity and mortality.

To date, lung disease in cystic fibrosis is mainly treated with a combination of antibiotics, anti-inflammatory agents, bronchodilators and mucolytics.

Cysteamine was shown to advantageously treat CF symptoms by reducing the thickness of mucus allowing it to be cleared away more easily (mucolytic activity), and, at the same time, by acting directly against the bacteria in the lungs (anti-bacterial activity).

Therefore, the overall multi-active properties of cysteamine (lowering the excessive mucus in the airways, killing the bacteria responsible for the recurrent respiratory infections and disrupting the biofilms in which they colonise) can be therapeutically beneficial in CF patients (see Graham Devereux et al. "Cysteamine as a Future Intervention in Cystic Fibrosis Against Current and Emerging Pathogens: A Patient-based ex vivo Study Confirming its Antimicrobial and Mucoactive Potential in Sputum", EBioMedicine (2015) 1507-1512; and Charrier et al., 2014: http://dx.doi.orq/10.1186/s13023-014-0189-2).

As a consequence of these findings, inhalable formulations of cysteamine for the treatment of lung diseases are needed. In fact, to better the effectiveness of cysteamine in the lungs, the drug is to be delivered as an aerosol directly in the patient's airways.

Pulmonary drug delivery possesses many advantages in terms of drug administration, such as non-invasive route of administration, lower metabolic activity, avoidance of first pass metabolism, prompt systemic absorption and, above all, high local drug concentration which allows to contrast lung mucosal infection/inflammation and to improve tissue healing. However, to face foreign particles entered in the body, the lungs present multiple clearance mechanisms (mucociliary transport, alveolar macrophages, absorptive and metabolic degradation) which, unfortunately, can act as barriers to inhaled drugs compromising the therapeutic efficacy thereof. Therefore, in order to limit the pulmonary clearance mechanisms and provide enhanced therapeutic effect and/or controlled drug release, particulate-based drug delivery systems have emerged as an innovative and promising alternative to conventional inhaled drug solutions.

US 2017/0348254, for instance, discloses microparticles of cysteamine bitartrate prepared by spray drying the active ingredient along with stabilizing agents such as trehalose and leucine. However, the aerodynamic performance of the obtained powder was low and the fine particle doses were minimal reporting, after aerosolization of an amount of spray dried powder approximately between 160 and 270 mg, a fine particle dose of cysteamine bitartrate only between 3 and 6.9 mg.

Therefore, considering this very low amount of drug deposited into lung after aerosolization of more than 100 mg of powder, an effective inhalable formulation of cysteamine having a high respirability is still needed.

Another issue to address is the instability of cysteamine in the solid state in view of the administration via inhalation. Unfortunately, inhalable pulmonary microparticles made with existing cysteamine salts (such as those described in US 2017/0348254), also in the optimum size range for lung delivery (1-5 µm), revealed very poor lung penetration, mainly due to the high sensitivity of the active ingredient to the environmental conditions. Said salts, in fact, are hygroscopic, deliquescent and prone to oxidative degradation. Besides, cysteamine salts known from commercially available products, such as hydrochloride and bitartrate, have unfavourable particle size that determines poor aerodynamic properties making said salts unsuitable for inhalation as dry powder formulation.

CN 101 367 884, in addition, discloses a thiolated hyaluronic acid conjugate covalently linking (amide bond) cysteamine and a preparation method thereof. The method comprises adding 1-ethyl-3-(3-dimethylamino propyl)-carbodiimide (EDAC) and N-hydroxysuccinimide (NHS) in the hyaluronic acid solution in order to activate the carboxylic group; then, adding cysteamine hydrochloride and lyophilizing the reaction mixture affords a drug/polymer conjugate useful as bioadhesive material for non-injectable preparations. However, the method involves both EDAC and NHS, reagents not recognized as safe for inhalation. Moreover, the conjugate is a new chemical entity that modify the recognized safety of cysteamine for human uses. Finally, the obtained conjugate being a lyophilized powder, is not even suitable for inhalation in dry powder inhalers.

Therefore, the use of cysteamine as dry powder for inhalation in the treatment of lung diseases, further requires the discovery of new stable and respirable dry derivatives of the drug.

DEFINITIONS

Figure 1:
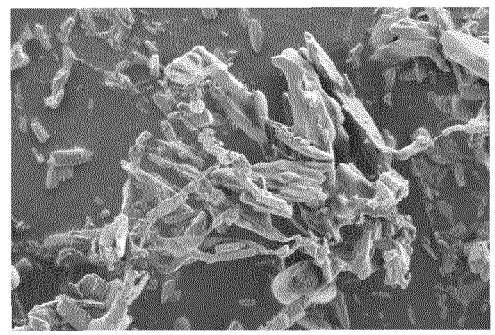
FIG. 1: SEM pictures of a) cysteamine base particles and b) cysteamine hyaluronate spray-dried microparticles. Spray-dried microparticles showed roundish structures and shrunken surface, whereas the cysteamine base shows particles similar to flakes.
Figure 1:
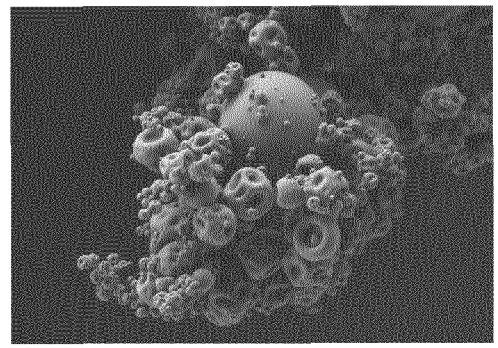

For the purpose of the present invention, the term "respirability" refers to the amount of drug deposited into the lungs with respect to the amount of powder to be aerosolized.

The term "Fine Particle Dose" (FPD) is the amount of drug in the delivered dose which particles have an aerodynamic diameter lower than 5 μm. These particles are capable of penetrating the lung during inhalation. The term "Fine Particle Fraction" (FPF) is the FPD expressed as a percentage of the delivered dose that is the amount of powder leaving the inhaler.

The term "median particle size" describes the particle diameter in μm where the particle size distribution is equally divided in two populations. For the purpose of the present invention, the median particle size is calculated on a volume distribution ($DV_{50}$).

The term "total capacity", when referred to an ion exchange resin, means the total number of available sites per weight unit to which a counterion can link for the ion exchange. It is expressed in milliequivalent per gram (meq/g).

The term "lung disease" includes any respiratory disease which affect the lungs such as, for example, cystic fibrosis and COPD.

The abbreviation "NaHA" means sodium hyaluronate, while "HA" means hyaluronic acid. The term "about", when referred to a value, means the stated value plus or minus 5% while, when referred to a range, means the outmost values plus or minus 5%.

DETAILED DESCRIPTION OF THE INVENTION

To date, a polymeric substance such as hyaluronic acid has never been employed for the preparation of new cysteamine salts.

HA is a natural occurring polysaccharide, consisting of a linear chain of D-glucuronic acid and N-acetylglucosamine, and it is an abundant constituent of the extracellular matrix of connective tissue, synovial fluid, embryonic mesenchyme and vitreous humor. Despite being known for its anti-inflammatory activity, hyaluronic acid has never been considered as counterion for making a salt of cysteamine. In fact, due to its poor acidity, HA in not expected to form a stable salt with the weak base cysteamine in solid form. Moreover, HA is commercially available in the form of sodium salt of hyaluronic acid which prevent HA to form a salt with the weak base cysteamine.

After extensive experimentations, the inventors of the present invention have now surprisingly found that is possible to easily obtain a cysteamine hyaluronate salt which is stable in solid form and can advantageously serve for making highly respirable microparticles.

Therefore, a first object of the present invention is a process for the preparation of cysteamine hyaluronate microparticles, said process comprising the following steps:
 a. Dissolving sodium hyaluronate.
 b. Adding an ion exchange resin.
 c. Filtering the obtained solution.
 d. Adding cysteamine base.
 e. Spray-drying the obtained solution.

In detail, step a. provides for the dissolution of sodium hyaluronate having a molecular weight between 22 kDa and 2 MDa, preferably between 30 kDa and 1 MDa, in a suitable solvent. Said solvent can be a polar solvent, preferably water. The pH value of the hyaluronate solution ranges between 6.1 and 6.9.

Step b. provides for the addition of an ion exchange resin, preferably a cation exchange resin, to the hyaluronate solution. In a preferred embodiment, a strong acid cation exchange resin is employed (e.g., Dowex Monosphere™ 650C (H) matrix of styrene-DVB gel and sulfonic acid as functional group). The strong cationic resin can be used in batch or in continuous mode. Preferably, the resin is used in batch mode meaning that the hyaluronate solution is put in direct contact with the resin for the time necessary to complete the ion exchange and then removed. In order to increase the contact between sodium hyaluronate and the resin, the solution can be kept under stirring for a suitable period of time such as, for example, from 1 to 3 hours. Therefore, free hyaluronic acid is obtained from the hyaluronate solution by exploiting the ability of the resin to exchange $H^+$ ions with $Na^+$ ions. The pH value of the obtained HA solution ranges between 2.2 and 2.8.

The exhausted resin is then removed from the HA solution by filtration (step c.). The term "filtration" is meant to encompass any filtration method known to those of ordinary skills in the art such as, for example, filtration by Buchner funnel or by membrane. After the recovery of the HA solution, cysteamine free base was added (step d.) affording the formation of a salt solution of cysteamine base/hyaluronic acid. The salt solution obtained in step d. has a weight ratio (w/w) cysteamine base:hyaluronic acid (as hyaluronate) ranging between 1:3 and 1:10, preferably between 1:5 and 1:8, more preferably about 1:7. The pH value of the obtained salt solution ranges between about 3.7 and 6.9.

The salt solution is finally subjected to spray-drying process (step e.). The spray drying was performed by means of a suitable spray dryer such as, for example, the Büchi mini spray dryer B-191 or B-290. For the purpose of the present invention, preferred, but not limiting, operational conditions ranges can be as follows: inlet temperature between 120 and 160° C., aspiration between 80 and 100%, feed rate between 2 and 6 mL/min and air flow rate between 400 and 700 L/h. In addition, nozzle cleaning interval was adjusted at level 5 (one pressure blow every 7 s). Advantageously, said drying step e. allows to readily obtain inhalable cysteamine hyaluronate microparticles.

Said microparticles, in fact, have a log normal size distribution, with a median particle size ($D_{V50}$) below 10 μm, preferably below 5 μm, and a standard deviation of the mean less than or equal to ±0.5 μm. The particle size distribution of the spray dried powders was determined by laser light scattering (SprayTec, Malvern, U.K.). Approximately 10 mg of the powder was dispersed in 20 ml solution of 0.1% (w/V) Span 80 in cyclohexane and sonicated for 5 min. Among the formulations #2 and #8, reported in Table 1, the values of $D_{V50}$ and standard deviation were 2.66±0.03 and 2.57±0.06, respectively.

The morphological characterization of the spray-dried microparticles was studied by scanning electron microscopy (SEM, SUPRA 40, Carl Zeiss NTS GmbH, Oberkochen, Del.). In detail, cysteamine base (FIG. 1 (a)) shows particles similar to flakes, whereas cysteamine hyaluronate spray-dried microparticles (b) show roundish structures with shrunken surface. This structure reveals that the salt particles are empty providing an important advantage for respirability, due to the low value of bulk density of the powder made by empty particles. The bulk density of the powders was determined according to Ph. Eur. last edition. The values of bulk density obtained were 0.24±0.02 g/cm$^3$ for powder #2 and 0.22±0.01 g/cm$^3$ for powder #8.

Additionally, the spray drying conditions provide a microparticles powder which is physically and chemically stable. As discussed above, cysteamine free base (pKa 9.42) is a molecule quite instable not only in solution but also as powder in environmental conditions. Hyaluronic acid, as salt counterion, stabilizes the thiolate amine. The resulting spray-dried microparticles powder for inhalation, due to the cysteamine embedding into polymeric structure of hyaluronic acid, is more resistant towards the environmental conditions of storage than other cysteamine salts.

In another aspect, the present invention relates to microparticles comprising cysteamine hyaluronate and optionally a pharmaceutically acceptable additive. To this extent, step d. can further comprise adding to the hyaluronic acid solution, additive(s) useful for improving particle shaping or increasing particle stability. Pharmaceutically acceptable additive(s), for example, can be selected from the group consisting of amino acids such as leucine, sugars as trehalose, or organic acids as ascorbic acid or acetic acid.

In yet another aspect, the present invention relates to coated microparticles of cysteamine hyaluronate. To this extent, step e. can provide for the concurrent spraying of two separated solutions, one of the active ingredient internally (inner orifice) and one of additive(s) externally (outer orifice) with respect to the nozzle. In detail, the inner orifice is feed with the cysteamine base/hyaluronic acid solution, while the outer orifice is feed with a solution comprising the additive(s). The two solutions are then concurrently but separately sprayed through a nozzle, preferably a coaxial nozzle, having a diameter ranging from 0.5 to 0.9 mm, preferably equal to 0.7 mm, allowing to obtain spray dried coated microparticles with uniform characteristics.

In a preferred embodiment, the selected additive is L-leucine. Leucine is known as lubricant suitable for the preparation of inhalable particles. According to the present invention, however, leucine, depositing externally, promotes a protective action over cysteamine hyaluronate thus increasing the physical/chemical stability of the cysteamine hyaluronate microparticles. In fact, the inventors have surprisingly found that leucine has the valuable property to counteract both the adhesiveness of hyaluronic acid and the hygroscopicity of cysteamine.

Microparticles according to a preferred embodiment of the invention comprise:
10 to 30% w/w of cysteamine,
50 to 80% w/w of hyaluronic acid, and
6 to 20% w/w of leucine.

The process according to the present invention allows to obtain a powder whose particles have size, density and shape suitable for the formation of a stable aerosol with a slow air flux. The obtained aerosol facilitates the transport of drug particles into the lungs by inhalation to reach, in a predictable and reproducible way, the bronchial and alveolar portion of the respiratory tract.

According to any aspect of the present invention, the respirable fraction (FPF) of the obtained microparticles powder can surprisingly reach values higher than 60%. This is particularly evident in the powders in which the additive leucine is added. Optimal results can be obtained when the coaxial nozzle is employed for spraying the leucine solution having a percentage of leucine higher than 10% w/v. Solutions with a lower concentration of leucine, instead, are more performant with the classical nozzle.

In another aspect, the present invention relates to a pharmaceutical composition comprising cysteamine hyaluronate microparticles according to the present invention. In yet another aspect, the present invention relates to the use of cysteamine hyaluronate microparticles or compositions thereof in a dry powder inhaler.

An important issue addressed and solved by the present invention is the provision of a new stable salt derivative of cysteamine. Advantageously, the process of the present invention allows to obtain a novel salt of cysteamine, which is cysteamine hyaluronate. Therefore, a further object of the present invention is the cysteamine hyaluronate salt.

The formation of the novel cysteamine hyaluronate salt through the process of the present invention was demonstrated by Fourier transform infrared (FT-IR) spectroscopy.

Figure 2A:
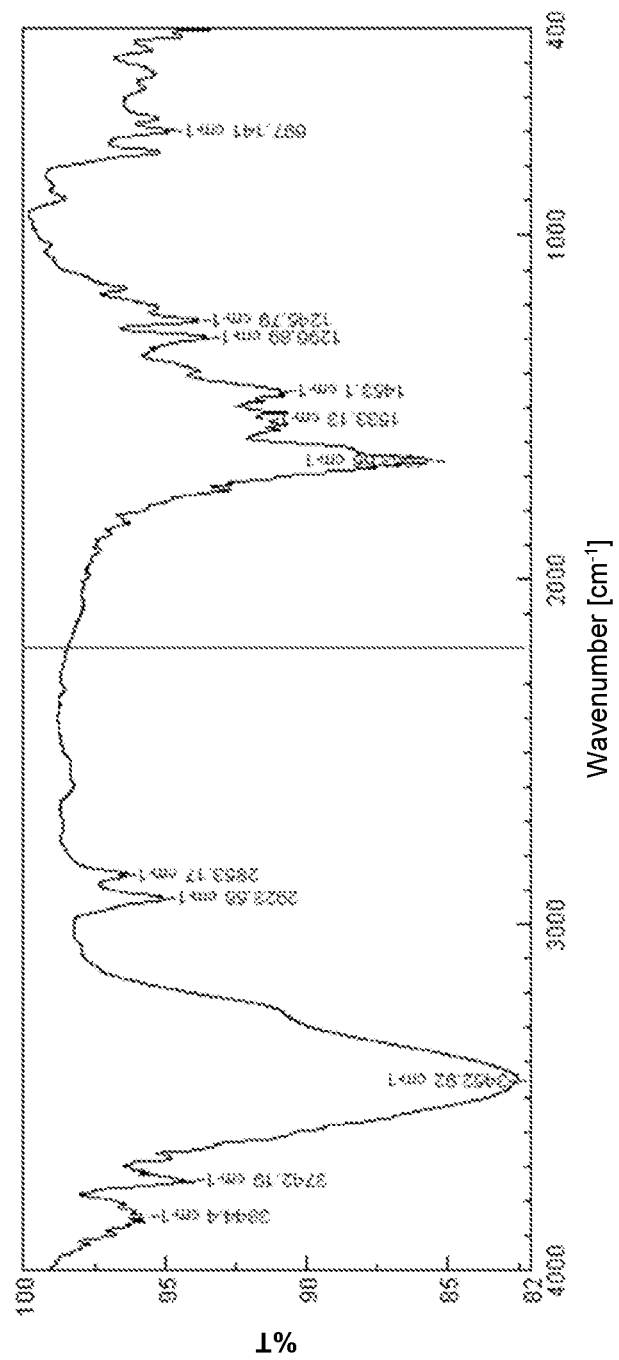
FIG. 2: FT-IR spectra of a) cysteamine base, b) sodium hyaluronate and c) hyaluronic acid spray-dried microparticles.
Figure 2B:
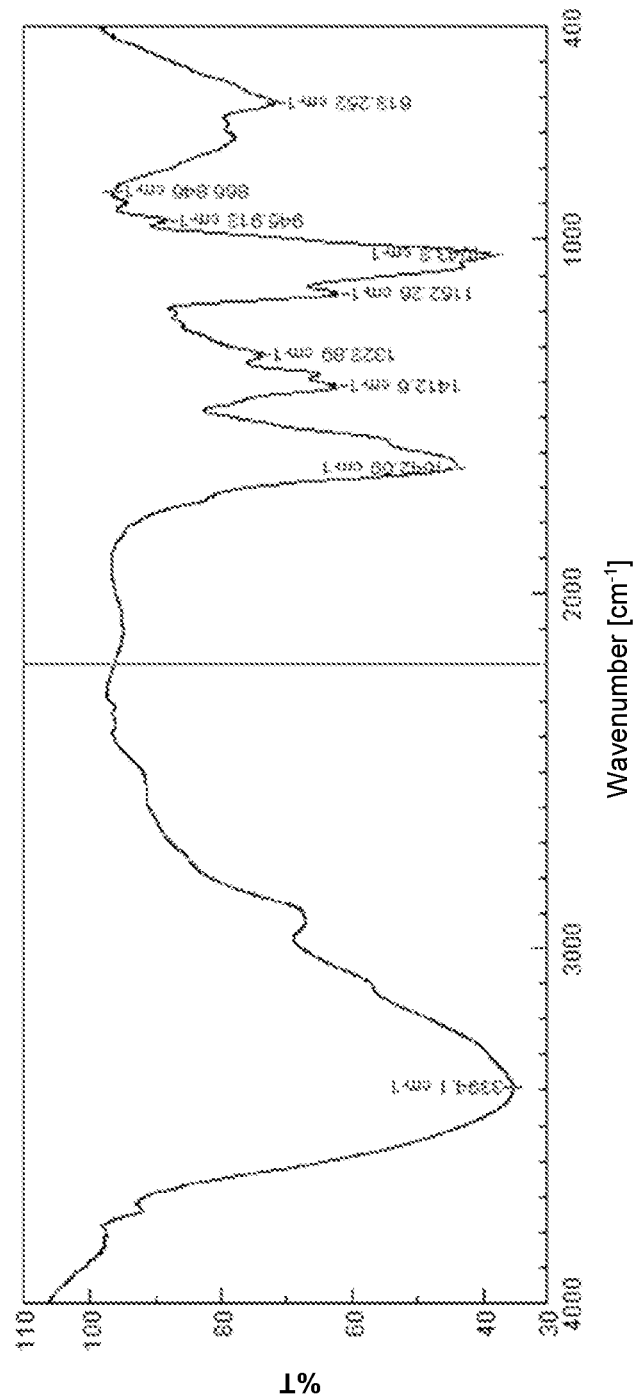
Figure 2C:
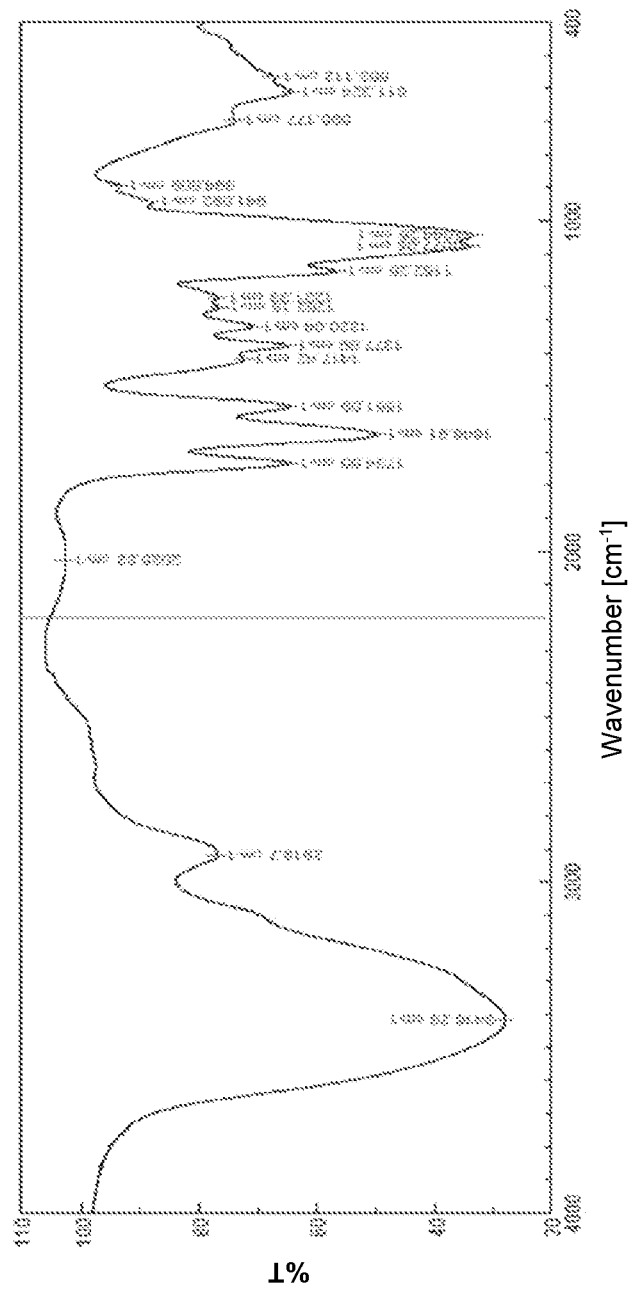

The FT-IR spectral measurements were taken at room temperature using Jasco FT/IR-460 Plus Jasco in transmittance mode in the wavenumber range of 4000-650 nm$^{-1}$. The analysed sample was prepared by dispersing the powder with KBr in ratio 1:9 (w/w) in a mortar and then compacting the blend with a hydraulic press. The FT-IR spectrum of hyaluronic acid spray-dried microparticles (FIG. 2 (c)) differs from that of sodium hyaluronate powder (b) by the presence of a fork band, made of three peak, attributed to the stretching vibration of the C=O peak of carboxylic group (1734 cm$^{-1}$), stretching vibration of the C=O peak of secondary amide group (1641 cm$^{-1}$) and NH deformation (II amide) (1561 cm$^{-1}$). Moreover, a variation in terms of intensities and shifts of the peaks at 1417, 1378 and 1320 cm$^{-1}$, with respect to the sodium hyaluronate, is observed. Finally, a difference is evident in the band at 1043 cm$^{-1}$, where the shoulder at 1077 cm$^{-1}$ becomes a peak.

Figure 3:
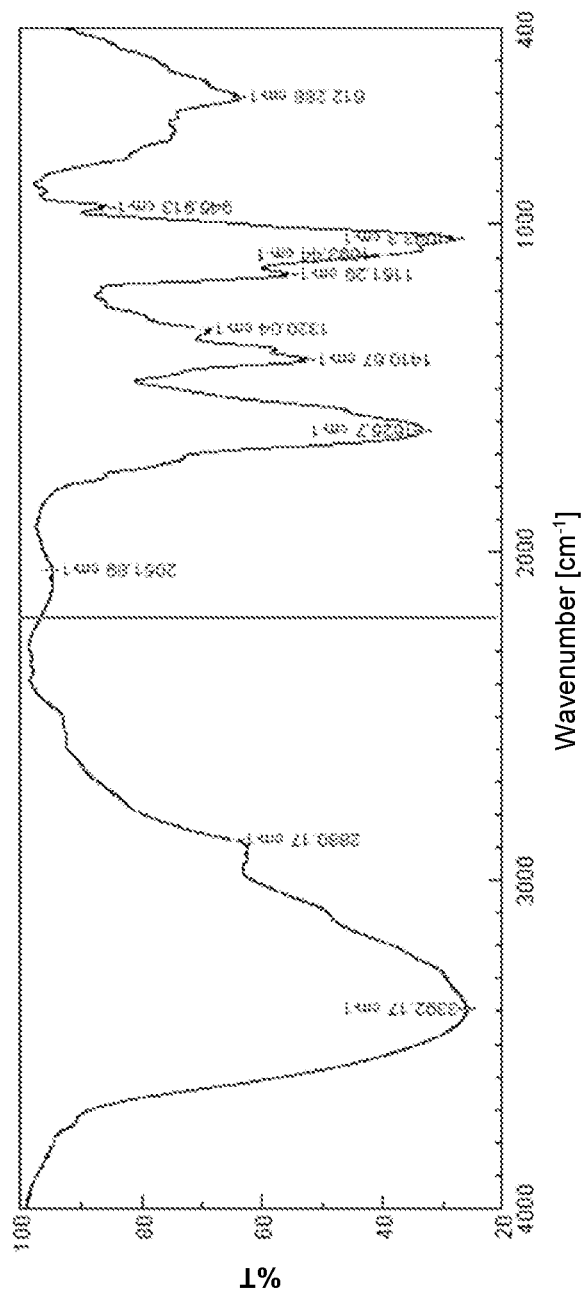
FIG. 3: FT-IR spectrum of cysteamine hyaluronate spray-dried microparticles.

Concerning the FT-IR spectrum of cysteamine hyaluronate spray dried powder (FIG. 3), the band at ~1645 cm$^{-1}$ corresponds both to the stretching of the —NH$_2$ group of cysteamine and the stretching of C=O of the carboxylic group of the hyaluronic acid. Compared to the FT-IR spectra of cysteamine free base and hyaluronic acid, a difference indicating an interaction of these functional groups in the cysteamine hyaluronate spray-dried powder is evident. Moreover, from the analysis of the FT-IR spectrum of cysteamine hyaluronate salt spray-dried powder, a reduction of intensity of the peak at 1370 cm$^{-1}$ (stretching vibration of the methyl group of hyaluronate), becoming the shoulder of the band at 1410 cm$^{-1}$, is observed. The intensity of the peak at 1077 cm$^{-1}$, corresponding to the stretching vibration of C—O of carboxylic group, is reduced as demonstrated by its transformation in a shoulder (as in the spectrum of the sodium hyaluronate). This further supports the interaction between cysteamine base and hyaluronic acid at the level of the carboxylic group of the hyaluronic acid and the amino group of the cysteamine.

Figure 4:
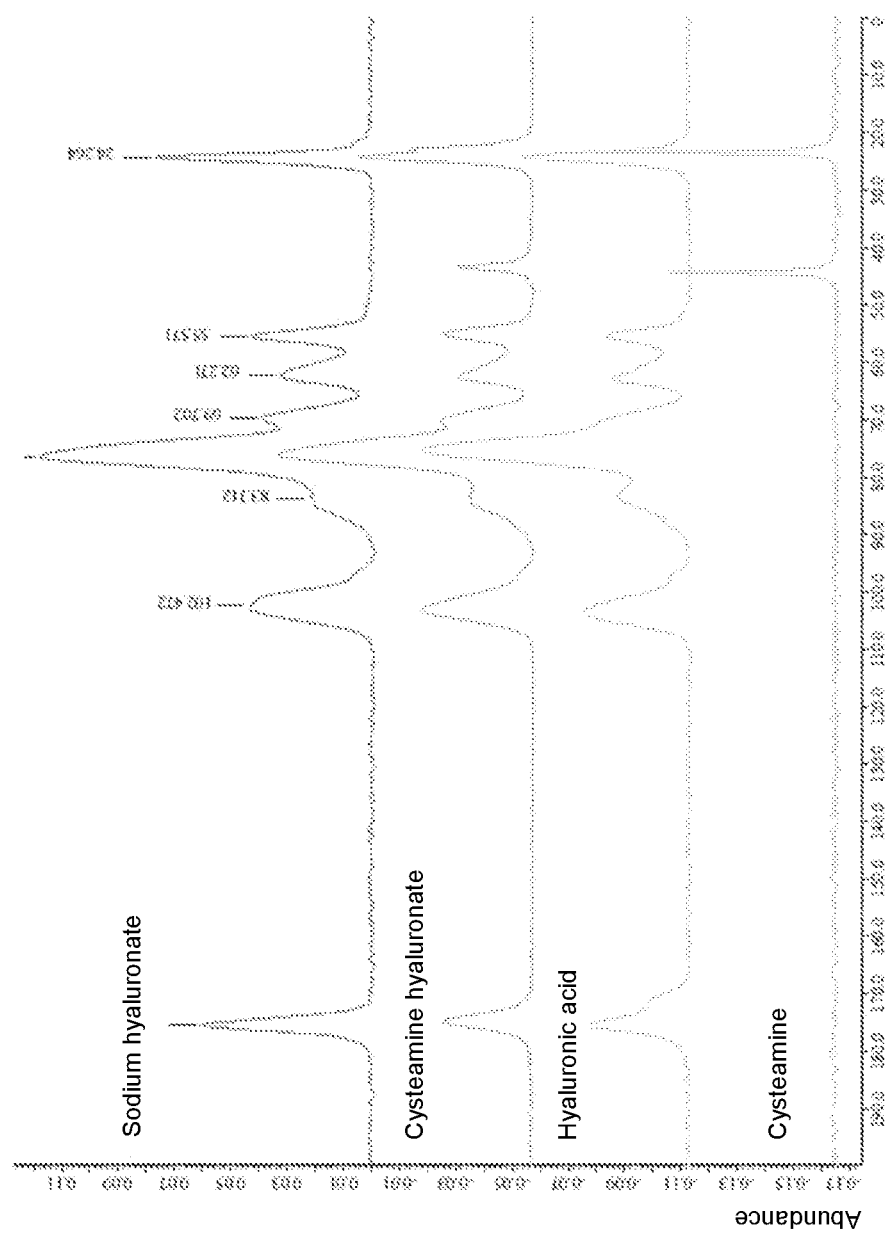
FIG. 4: $^{13}$C-NMR spectra of sodium hyaluronate, cysteamine hyaluronate spray-dried microparticles, hyaluronic acid spray-dried powder and cysteamine base. Comparing the spectrum of cysteamine hyaluronate with the others, the salt formation is clearly evidenced by the presence of peaks of both the counterions, hyaluronic acid and cysteamine. However, the spectrum of cysteamine hyaluronate spray-dried microparticles shows differences compared to the spectra of the counterions alone and of the sodium hyaluronate.

The formation of the novel cysteamine hyaluronate salt was further investigated by $^{13}$C-NMR analysis in solid state. The spectra of cysteamine free base, sodium hyaluronate, hyaluronic acid spray-dried powder and cysteamine hyaluronate spray-dried powder were collected with JNM-ECZR 400 NMR spectrometer (Jeol, Peabody, USA) in solid mode. Comparing the spectrum of cysteamine hyaluronate with the others, the salt formation is clearly evidenced by the presence of peaks of both the counterions (FIG. 4), with a small shift of these peaks due to the influence of the different neighbours compared to the counterions alone (hyaluronic acid and cysteamine). Moreover, significant differences are observed in the spectra of sodium hyaluronate and hyaluronic acid. In particular, in the spectrum of hyaluronic acid a shoulder appears on the peak at about 175 ppm and the peak at about 69 ppm, that is present in the sodium hyaluronate spectrum, disappears.

Cysteamine hyaluronate is stable at environmental conditions, not prone to oxidative degradation, non-hygroscopic and non-deliquescent.

In fact, after a month at 25° C./60% R.H. the chemical stability by HPLC analysis and the physical stability by in vitro respirability test were assessed. No variation, with respect to cysteamine hyaluronate spray-dried powder at time 0, was observed in terms of content of cysteamine impurities and fine particle fraction.

Moreover, sodium hyaluronate was found to limit the multiple pulmonary clearance mechanisms, allowing to obtain a more effective and prolonged therapeutic effect on the lungs of a carried drug (see Ibrahim M. El-Sherbiny et al. "Inhaled nano- and microparticles for drug delivery", Glob Cardiol Sci Pract (2015), 2, 1-14). Thus, the therapeutic effect of the cysteamine hyaluronate salt has to be assigned to both the cysteamine and the hyaluronic moieties.

Therefore, the inventors have surprisingly found a new salt of cysteamine that overcomes the drawbacks of those known in the art not only because of the advantageous chemical/physical characteristics, but also because of the more effective and prolonged therapeutic effect on the lung epithelium.

The present invention further provides for cysteamine hyaluronate for use as a medicament, in particular in the treatment of lung diseases, more in particular in the treatment of cystic fibrosis infection conditions.

In conclusion, the manufacturing process of the present invention allows to obtain a stable salt derivative of cysteamine, i.e., cysteamine hyaluronate, already in the form of readily inhalable microparticles.

DESCRIPTION OF THE PREFERRED EMBODIMENTS

The embodiments herein described have illustrative purpose only and are not meant to limit the scope of the present invention. Moreover, modifications and alterations of the embodiments below, obvious to a man skilled in the art, are intended to be encompassed by the attached claims.

Characterization of spray-dried microparticles of cysteamine hyaluronate Starting from sodium hyaluronate 0.35 MDa (#2-#6) or 0.9 MDa (#1), spray-dried powders of cysteamine hyaluronate, with or without additive(s), have been prepared according to the present invention (Table 1). The use of sodium hyaluronate at different molecular weight does not adversely affect the properties of the final product, in terms of cysteamine assay, bulk density and particle size distribution of the spray-dried powder.

TABLE 1

Compositions of spray-dried powders of cysteamine.

| Formulation | Composition (%, w/w) | Spray-dryer parameters | Yield (%) | Residual water (%) | Cysteamine content (%) | FPF (%) |
|---|---|---|---|---|---|---|
| #1 | 12.9 cysteamine<br>87.1 NaHA | B290, $T_{inlet}$ 150° C., $T_{outlet}$ 75° C., Feed rate 5 ml/min | 62.5 | 7.35 | 13.4 | 29.0 |
| #2 | 12.2 cysteamine<br>87.8 NaHA | B191, $T_{inlet}$ 120° C., $T_{outlet}$ 62° C., Feed rate 5 ml/min | 68.1 | 8.4 | 10.4 | 22.8 |
| #3 | 12.7 cysteamine<br>87.1 NaHA<br>0.2 ascorbic acid | B191, $T_{inlet}$ 120° C., $T_{outlet}$ 64° C., Feed rate 5 ml/min | 24 | 7.9 | 10.8 | 31.8 |
| #4 | 15 cysteamine<br>85 NaHA<br>0.8 mL acetic acid | B290, $T_{inlet}$ 120° C., $T_{outlet}$ 58° C., Feed rate 5 ml/min; | 64.2 | 7.5 | 12.7 | 27.0 |
| #5 | 12.8 cysteamine<br>78.5 NaHA<br>8.7 L-leucine | B290, $T_{inlet}$ 120° C., $T_{outlet}$ 60° C., Feed rate 5 ml/min | 66.1 | 5.9 | 10.9 | 65.9 |
| #6 | 13.1 cysteamine<br>78.2 NaHA<br>8.7 L-leucine | B290, $T_{inlet}$ 120° C., $T_{outlet}$ 63° C., Feed rate 4 ml/min; coaxial nozzle | 44.3 | 7.3 | 11.2 | 33.4 |
| #7 | 13.4 cysteamine<br>69.1 NaHA<br>17.5 L-leucine | B290, $T_{inlet}$ 120° C., $T_{outlet}$ 62° C., Feed rate 4 ml/min; coaxial nozzle | 61.1 | 6.0 | 11.4 | 62.3 |
| #8 | 12.1 cysteamine<br>70.2 Na HA<br>17.7 L-leucine | B290, $T_{inlet}$ 150° C., $T_{outlet}$ 75° C., Feed rate 4 ml/min; coaxial nozzle | 60.8 | 5.8 | 10.3 | 69.8 |

The amount of residual water was assessed by thermogravimetric analysis (TGA) in the temperature range from 25° C. to 150° C.

The content of cysteamine in the spray-dried powders was determined by HPLC analysis, in gradient mode. In detail, HPLC was equipped with Shimadzu LC-10AT chromatograph, provided with LC-10AS pumps and SPD-10A UV-VIS spectrometer. C18 column was used as stationary phase, while the mobile phase was composed of solvent A (11.52 g of sodium dodecyl sulphate dissolved in 380 ml of Milli-Q grade water/300 ml of acetonitrile/320 ml of methanol and 1.4 ml of $H_3PO_4$ 85% v/v) and solvent B (acetonitrile), mixed with gradient method at flow rate of 1.4 ml/min. The detection wavelength was set at 210 nm.

The value of the powder respirability for the application as inhalable powders were characterized in terms of aerodynamic diameter determination.

In vitro aerodynamic assessment of the spray dried powders obtained according to the present invention was carried out using the Fast Screening Impactor (FSI) (Copley Scientific, UK). The FSI classifies the powder discharged from the inhaler into two aerodynamic particle fractions, namely a coarse fraction and a fine fraction (aerodynamic diameter higher and lower than 5 μm, respectively). The Coarse Fraction Collector (CFC) is equipped with the insert that enables a specific cut-off size at 60 L/min: all particles above 5 μm are collected, while all particles below that size pass through. The particles not captured in the CFC constitute the respirable fraction of the aerosolized powder and keep following the airstream. They are all captured by the subsequent fine fraction collector (FFC) e.g., a filter (type NE glass filter, 76 mm (Pall 183 Corporation, USA)).

In order to measure the respirability, an accurately weighed amount of spray-dried powder (about 20 mg) was manually introduced into a size 3 hard HPMC capsule. The capsule was inserted into the holder chamber of the dry powder device (RSO1®, Plastiape Spa, Osnago LC, Italy) and pierced. The device was connected to the FSI and activated by air stream for 4 sec at 60 L/min (corresponding to pressure drop 4 kPa for this inhaler). Therefore, the percentage of cysteamine deposited in the FFC filter versus the amount loaded in the capsule, also defined as fine particle fraction (FPF), was quantified by HPLC analysis. Each powder was tested in duplicate.

Figure 5:
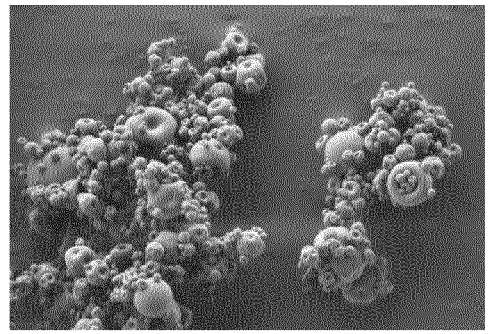
FIG. 5: SEM images of cysteamine hyaluronate spray-dried microparticles:
 a) Formulation #2: 2.2% cysteamine/87.8% sodium hyaluronate.
 b) Formulation #5: 13.1% cysteamine/78.2% sodium hyaluronate/8.7% L-leucine.
 c) Formulation #7: 13.4% cysteamine/69.1% sodium hyaluronate/17.5% L-leucine.
 d) Formulation #8: 12.1% cysteamine/70.2% sodium hyaluronate/17.7% L-leucine.
Figure 5:
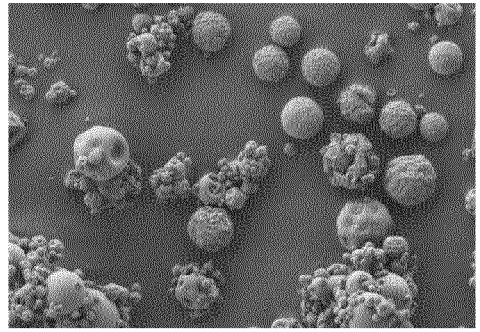
Figure 5:
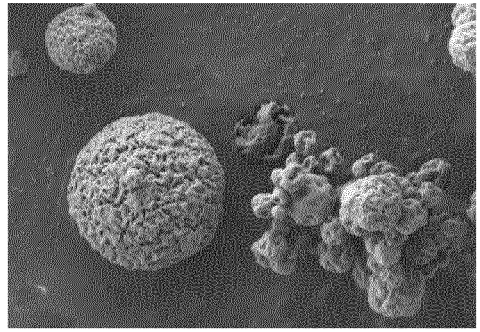
Figure 5:
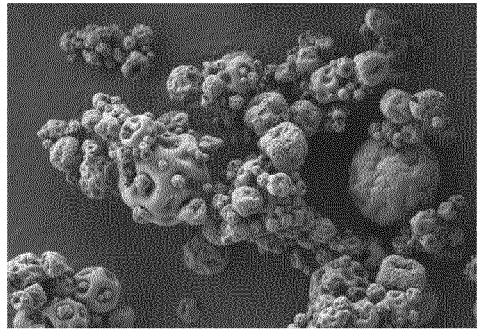

The morphological characterization of the cysteamine hyaluronate spray-dried microparticles was performed by scanning electron microscopy (SEM). Spray-dried microparticles show both roundish structures and small shrunken surface. In particular, when the L-leucine solution was sprayed from the outer orifice of the coaxial nozzle, spongy microparticles were obtained (FIG. 5 b-d). This particle shape can reduce the contact between the particles making their performance in terms of aerosolization more efficient.

EXAMPLES

Capacity of hyaluronic acid solution to react with a base 25 ml of the hyaluronic acid solution, containing 63.25 mg of NaHA 0.35 MDa were titrated using as indicator bromothymol blue. The titrant (0.01 N NaOH solution) was slowly added until the indicator changed color from yellow to blue (pH around 7.0). The neutralization of HA solution required 12.13 ml of 0.01N NaOH (i.e., 0.1213 meq); thus, 63.25 mg of NaHA 0.35 MDa on average contains 0.1213 milliequivalents of HA. Therefore, the amount of cysteamine base (MW 77.15) that can react with the hyaluronic acid obtained from 63.25 mg of sodium hyaluronate, was calculated as follows: 0.1213×77.15=9.358 mg.

The weight ratio of cysteamine base:hyaluronic acid (as sodium hyaluronate MW 0.35 MDa) in the solution was about 1:7 w/w.

The solutions for spray drying were prepared according to this estimated calculation.

Preparation of Spray-Dried Microparticles of Cysteamine Hyaluronate

Example #1

500 mg of sodium hyaluronate (MW 0.9 MDa) were introduced in a flask containing 170 ml of depurated water at 50° C. under magnetic stirring. Then, considering that the capacity of the Dowex Monosphere 650C (H) resin is 2 meq/ml (density 1.22 g/ml), 500 mg of resin were added to the hyaluronate solution and left in contact at room temperature under magnetic stirring for about two hours until the pH value was stable (pH 3.03). The obtained solution containing hyaluronic acid was filtered using a Buchner funnel and collected in a 200 ml volumetric flask. The resin remained on the filter was washed with 10 ml of depurated water to extract the residual hyaluronic acid on the resin and funnel. After that, 74 mg of cysteamine base were dissolved in the HA flask under mixing to afford a salt solution of cysteamine/hyaluronic acid, and the volumetric flask was brought to volume with depurated water.

The weight ratio of cysteamine base:hyaluronic acid (as sodium hyaluronate MW 0.35 MDa) in the solution was about 1:7 w/w.

The solutions obtained as above disclosed were then subjected to spray-drying. The operational conditions of the spray-dryer (Büchi mini B-290) were settled as follows:

| | |
|---|---|
| T inlet (° C.) | 150 |
| T outlet (° C.) | 75 |
| Aspiration (%) | 100 |
| Feed rate (ml/min) | 5 |
| Airflow (L/h) | 600 |

The yield of the process was 62.5%. The content of drug in the spray-dried microparticles was determined by HPLC analysis. The powder obtained had a cysteamine content of 13.4±1.5%. The residual water of the powder was performed by thermogravimetric analysis (TGA) in the temperature range from 25 to 150° C. The powder had a water content of 7.35%.

Examples #3-#4-5 #

Cysteamine hyaluronate spray-dried microparticles comprising an additive were prepared according to Example #1 with the only difference that the additive is further added to the hyaluronic acid solution, obtained as above disclosed, before the addition of cysteamine base.

Example #6

Cysteamine hyaluronate spray-dried microparticles comprising the additive leucine were manufactured by spray drying the cysteamine/hyaluronic acid salt solution prepared modifying the method reported for Example #5. In detail, sodium hyaluronate was introduced in a flask containing 80 ml of depurated water at 50° C. under magnetic stirring. Then, the resin was added to the hyaluronate solution and left in contact at room temperature under magnetic stirring for about two hours until the pH value was stable. The obtained solution containing hyaluronic acid was filtered using a Buchner funnel and collected in a 100 ml volumetric flask. The resin remained on the filter was washed with 10 ml of depurated water to extract the residual hyaluronic acid on the resin and funnel. After that, the cysteamine base was dissolved in the HA flask, under mixing to afford a salt solution of cysteamine/hyaluronic acid, and the volumetric flask was brought to volume with depurated water.

The additive solution was prepared by dissolving leucine in a 100 ml volumetric flask with depurated water.

The additive solution was added to the cysteamine/hyaluronic acid solution during the spray-drying process by using a coaxial nozzle in which the two solutions of drug and additive were kept separate and sprayed in such a way that the solution stream leaving from the nozzle is made by an internal stream of cysteamine/hyaluronic acid salt solution (concentration 0.46% w/v) and an external stream of leucine solution (concentration 0.04% w/v).

The invention claimed is:

1. A process for the preparation of cysteamine hyaluronate microparticles comprising:
   a. Dissolving sodium hyaluronate:
   b. Adding an ion exchange resin:
   c. Filtering the obtained solution:
   d. Adding cysteamine base: and
   e. Spray-drying the obtained solution.

2. The process according to claim 1, wherein the solution obtained in step d. has a weight ratio cysteamine base: hyaluronic acid ranging between 1:3 and 1:10.

3. The process according to claim 1, wherein step d. further comprises the addition of a pharmaceutically acceptable additive.

4. The process according to claim 1, wherein step e. provides for the concurrent spray from a nozzle having an inner orifice and an outer orifice of a solution comprising cysteamine hyaluronate from the inner orifice and a solution comprising an additive from the external orifice of the nozzle.

5. The process according to claim 3, wherein said additive is selected from the group consisting of leucine, trehalose, ascorbic acid and acetic acid.

6. The process according to claim 5, wherein said additive is leucine.

7. Microparticles comprising cysteamine hyaluronate salt.

8. Microparticles according to claim 7, having a mean particle size below 5 µm.

9. Microparticles according to claim 7, having a FPF higher than 60%.

10. A pharmaceutical composition comprising microparticles according to claim 7.

11. A powder inhaler comprising the microparticles of claim 7.

12. A cysteamine salt, wherein said salt is cysteamine hyaluronate.

13. A method for the treatment of lung diseases, comprising administering cysteamine hyaluronate as an aerosol directly to the airways of a patient in need of such treatment.

14. A method for the treatment of cystinosis, comprising administering cysteamine hyaluronate to a patient in need of such treatment.

15. The process according to claim 2, wherein the cysteamine base:hyaluronic acid weight ratio is between 1:5 and 1:8.

16. The process according to claim 14, wherein the cysteamine base:hyaluronic acid weight ratio is 1:7.

17. The method of claim 13, wherein the lung disease is cystic fibrosis.

* * * * *